US008808252B1

(12) United States Patent
Fox

(10) Patent No.: US 8,808,252 B1
(45) Date of Patent: Aug. 19, 2014

(54) SYRINGE ASSEMBLY

(76) Inventor: Kevin T. Fox, Asheville, NC (US)

( * ) Notice: Subject to any disclaimer, the term of this patent is extended or adjusted under 35 U.S.C. 154(b) by 157 days.

(21) Appl. No.: 13/438,908

(22) Filed: Apr. 4, 2012

(51) Int. Cl.
*A61M 5/315* (2006.01)

(52) U.S. Cl.
USPC ............................ 604/227; 604/220; 604/218

(58) Field of Classification Search
USPC ................. 604/218, 220, 227, 229, 6.12, 187
See application file for complete search history.

(56) References Cited

U.S. PATENT DOCUMENTS

| | | | | |
|---|---|---|---|---|
| 2,295,849 A | * | 9/1942 | Kayden | .......................... 604/136 |
| 4,324,241 A | | 4/1982 | Reese | |
| 5,120,311 A | * | 6/1992 | Sagstetter et al. | ............ 604/110 |
| D383,839 S | | 9/1997 | Sullivan | |
| 5,830,152 A | | 11/1998 | Tao | |
| 2007/0073224 A1 | * | 3/2007 | Dries | ............................. 604/110 |
| 2012/0203183 A1 | * | 8/2012 | Tootoonchi | .................... 604/189 |

\* cited by examiner

*Primary Examiner* — Rebecca E Eisenberg

(57) ABSTRACT

A syringe assembly includes a barrel that has a first end and a second end. Each of the first and second ends is open. A needle hub is fluidly coupled to and extends away from the second end. A plunger extends into the first end and includes an internal end positioned within the barrel and an external end positioned distal to the barrel. A longitudinal axis is defined extending through the external end and the second end. A needle is fluidly coupled to and extends away from the needle hub. A grip is attached to the plunger. The grip is engaged by a person's finger to urge the plunger into the barrel. The grip has an outward portion extending outwardly away from the plunger and away from the longitudinal axis. The outward portion extends generally toward the barrel.

3 Claims, 4 Drawing Sheets

SYRINGE ASSEMBLY

BACKGROUND OF THE DISCLOSURE

Field of the Disclosure

The disclosure relates to syringe devices and more particularly pertains to a new syringe device for allowing actuation of a plunger with a person's index finger.

SUMMARY OF THE DISCLOSURE

An embodiment of the disclosure meets the needs presented above by generally comprising a barrel that has a first end and a second end. Each of the first and second ends is open. A needle hub is fluidly coupled to and extends away from the second end.

A plunger extends into the first end and includes an internal end positioned within the barrel and an external end positioned distal to the barrel. A longitudinal axis is defined extending through the external end and the second end. A needle is fluidly coupled to and extends away from the needle hub. A grip is attached to the plunger. The grip is configured to be engaged by a person's finger to urge the plunger into the barrel. The grip has an outward portion extending outwardly away from the plunger and away from the longitudinal axis. The outward portion extends generally toward the barrel.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
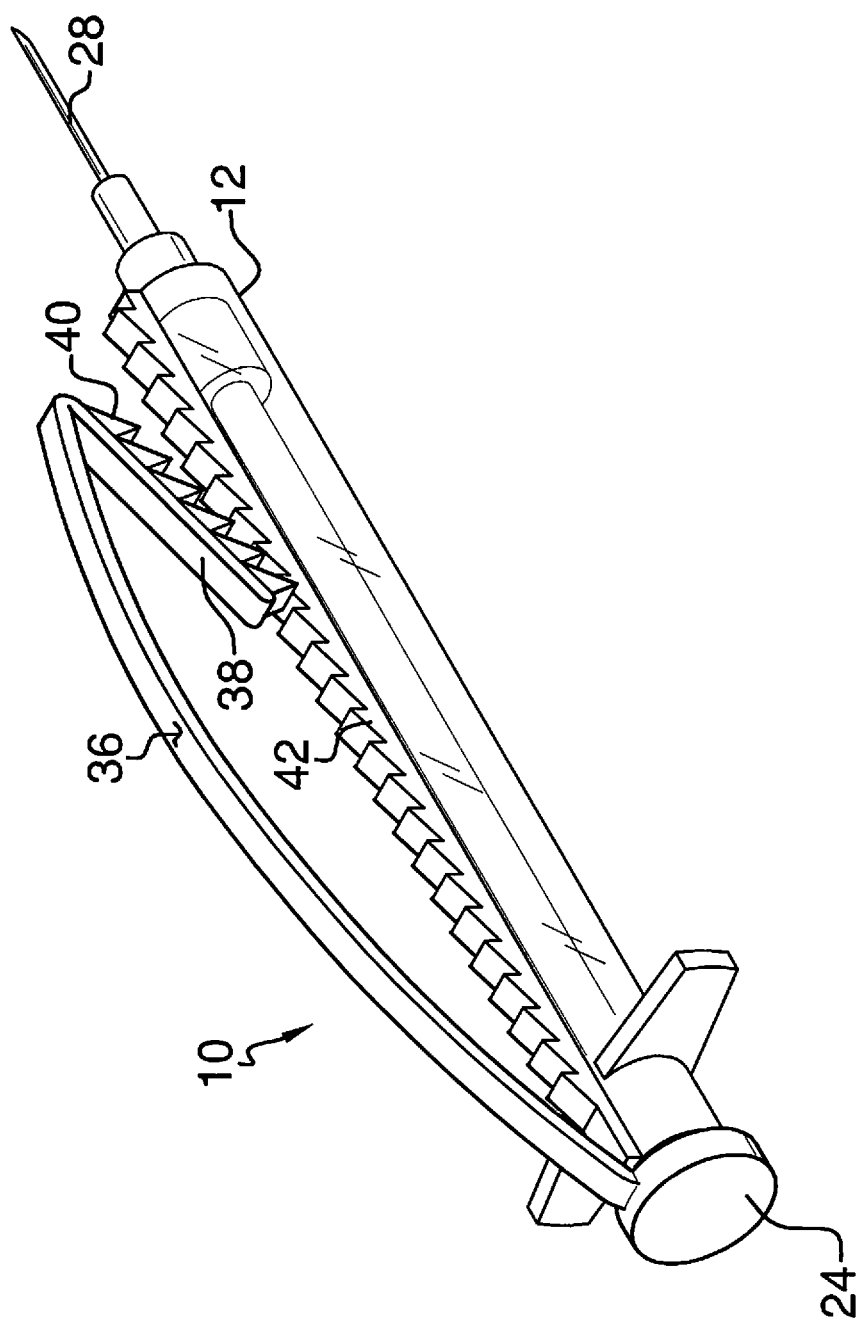
FIG. 1 is a rear perspective view of a syringe assembly according to an embodiment of the disclosure.
Figure 2:
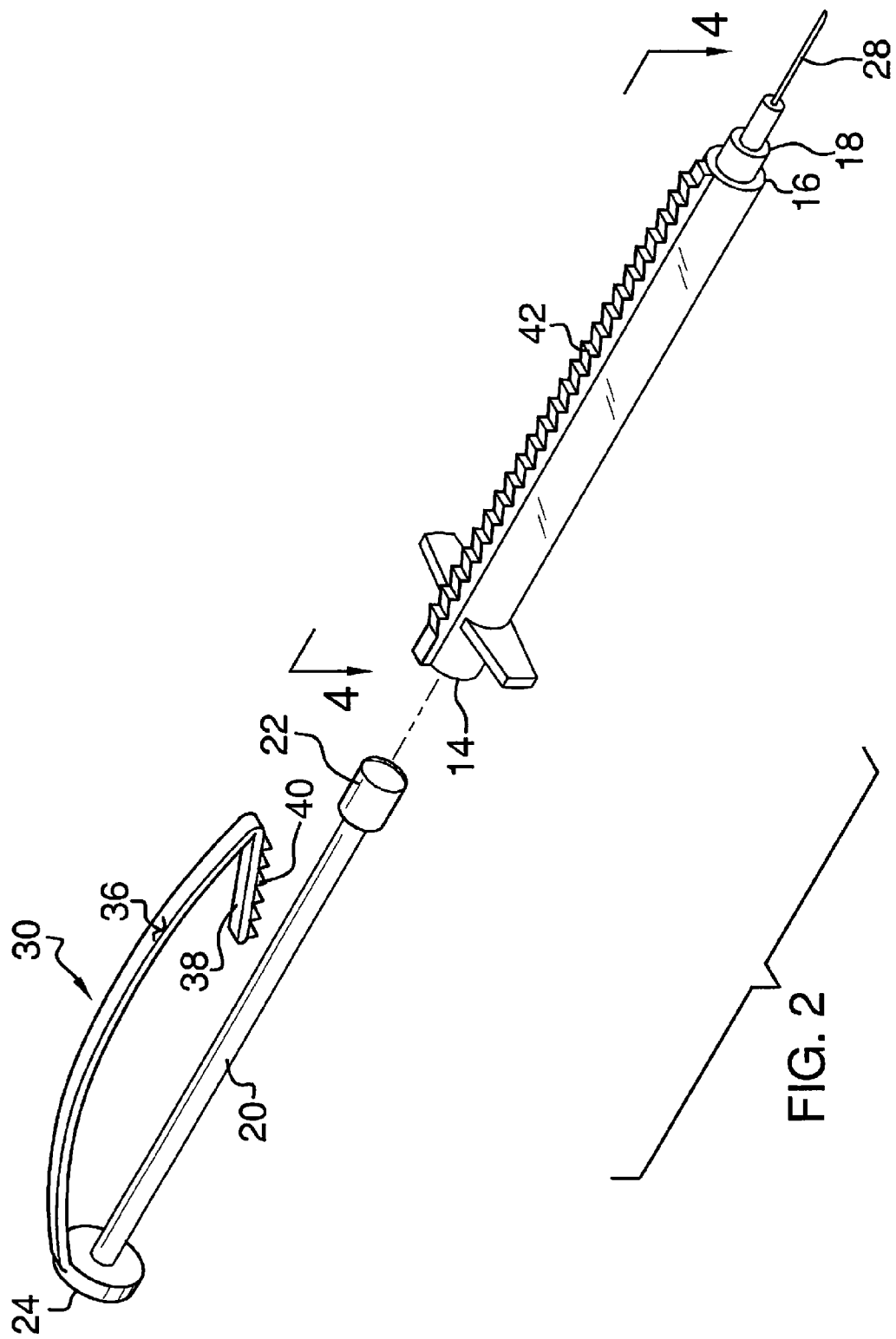
FIG. 2 is a front view of an embodiment of the disclosure.
Figure 3:
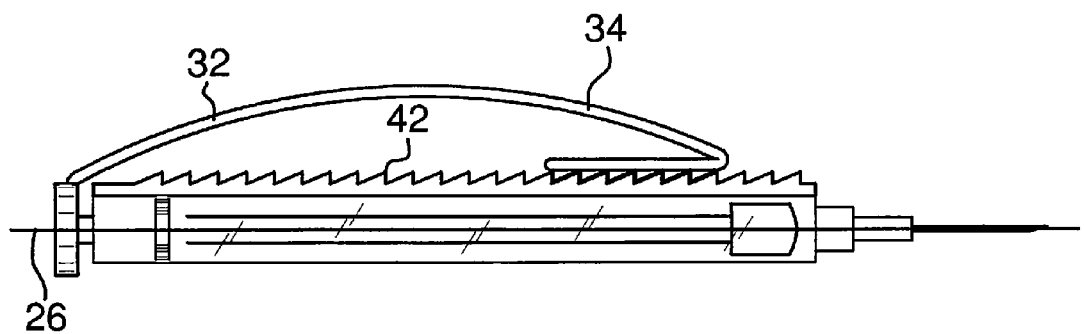
FIG. 3 is a side view of an embodiment of the disclosure.
Figure 4:
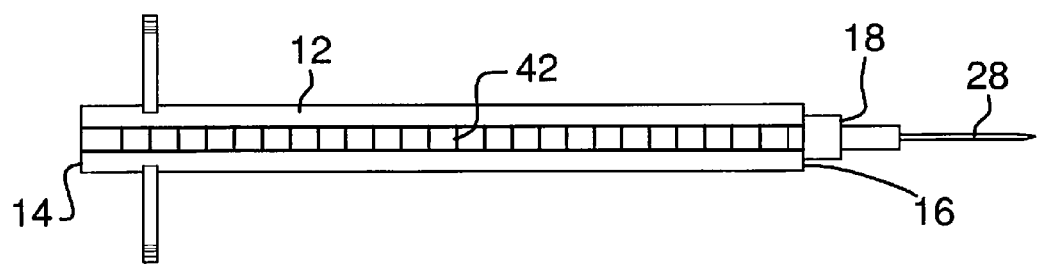
FIG. 4 is a top view of an embodiment of the disclosure having a plunger thereof removed.

With reference now to the drawings, and in particular to FIGS. 1 through 5 thereof, a new syringe device embodying the principles and concepts of an embodiment of the disclosure and generally designated by the reference numeral 10 will be described.

As best illustrated in FIGS. 1 through 5, the syringe assembly 10 generally comprises a barrel 12 having a first end 14 and a second end 16, wherein each of the first 14 and second 16 ends is open. A needle hub 18 is fluidly coupled to and extends away from the second end 16. A plunger 20 extends into the first end 14. The plunger 20 includes an internal end 22 positioned within the barrel 12 and an external end 24 positioned distal to the barrel 12. The external end 24 may comprise a plate, as shown in the Figures, a loop, or other structure designed to increase the friction between a person's fingers and the plunger 20. However, for purposes herein, the external end 24 will not define a grip for the reasons stated below. A longitudinal axis 26 is defined that extends through the external end 24 and the second end 16. A needle 28 is fluidly coupled to and extends away from the needle hub 18. The barrel 12, needle hub 18, plunger 20 and needle 28 are all conventional with respect to a typical syringe.

Figure 5:
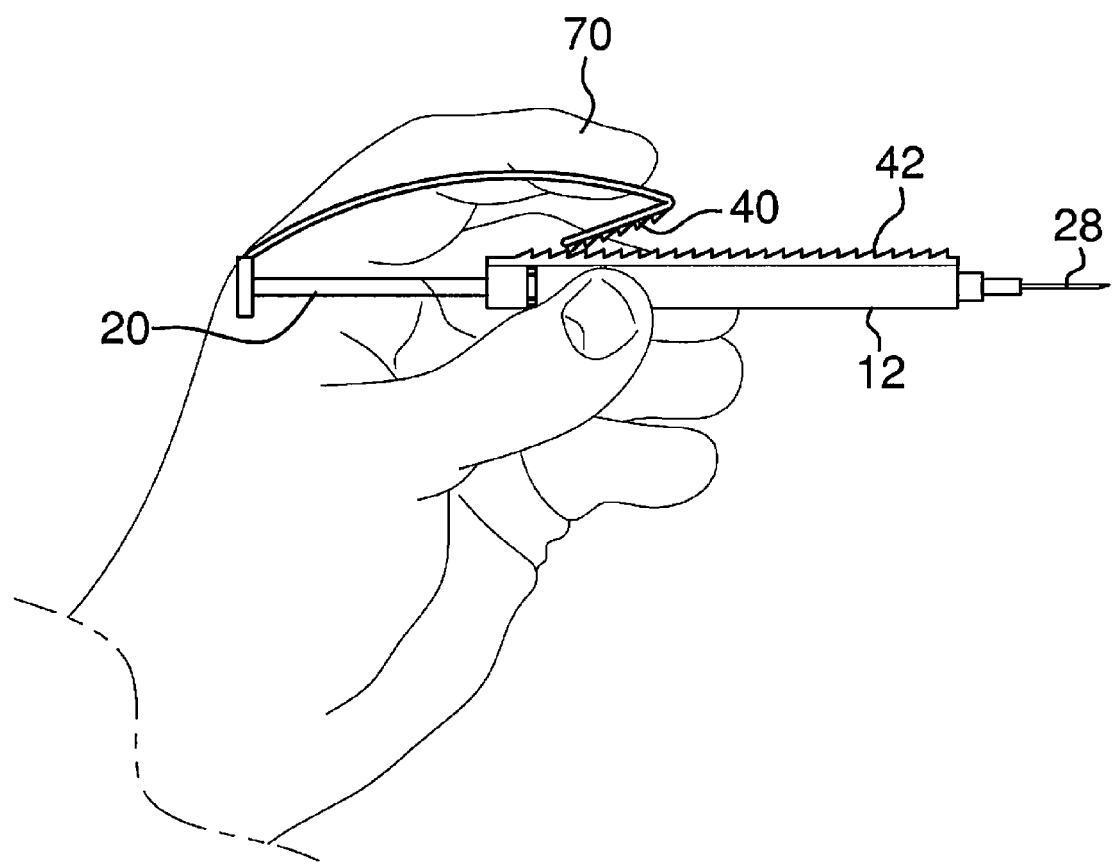
FIG. 5 is a side in-use view of an embodiment of the disclosure.

A grip 30 is attached to the plunger 20. The grip 30 is configured to be engaged by a person's finger 70 to urge the plunger 20 into the barrel 12. The grip 30 has an outward portion 32 extending outwardly away from the plunger 20 and away from the longitudinal axis 26. The outward portion 32 extends generally toward the barrel 12 and therefore is separate from the types of grip facilitating means discussed above with respect to conventional syringes. The grip 30 further has a return portion 34 extending toward the barrel 12 and toward the longitudinal axis 26. The outward 32 and return 34 portions each have an outer surface 36 facing away from the plunger 20 and the barrel 12. The outer surface 36 is convexly arcuate as is shown in FIG. 5. The grip 30 may be comprised of resiliently bendable material such as a plastic. The grip 30 allows a person to use their index finger 70, as opposed to their thumb, for actuating the plunger 20 to more precisely move the plunger 20.

A return section 38 is attached to an end of the return portion 34 opposite of the outward portion 32. The return section 38 extends toward the first end 14. The return section 38 has a plurality of first teeth 40 thereon extending toward the barrel. A plurality of second teeth 42 is positioned on the barrel 12. The second teeth 42 are positioned along a line extending between the first 14 and second 16 ends and are more particularly positioned such that the second teeth 42 engage the first teeth 40. The first 40 and second 42 teeth are angled to encourage movement of the return section toward the second end 16 and inhibit movement of the return section toward the first end 14.

In use, the assembly 10 is used in a conventional manner to administer medications and the like. However, the grip 30 has a particular shape to allow the user of the syringe assembly 10 to utilize their index finger 70, as shown in FIG. 5, for actuating the plunger 20 in a more precise manner. The first 40 and second 42 teeth prevent the plunger 20 from moving backwards due to back pressure.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A syringe assembly comprising:
a barrel having a first end and a second end, each of said first and second ends being open;
a needle hub being fluidly coupled to and extending away from said second end;
a plunger extending into said first end, said plunger including an internal end positioned within said barrel and an external end positioned distal to said barrel, a longitudinal axis being defined extending through said external end and said second end;
a needle being fluidly coupled to and extending away from said needle hub;
a grip being attached to said plunger, said grip being configured to be engaged by a person's finger to urge said plunger into said barrel, said grip having an outward portion extending outwardly away from said plunger and away from said longitudinal axis, said outward portion extending generally toward said barrel, wherein said grip has a return portion extending toward said barrel and toward said longitudinal axis;
a return section being attached to an end of said return portion opposite of said outward portion, said return section extending toward said first end, said return section having a plurality of first teeth thereon extending toward said barrel; and
a plurality of second teeth being positioned on said barrel, said second teeth being positioned along a line extending between said first and second ends, said second teeth engaging said first teeth.

2. The syringe assembly according to claim 1, wherein said first and second teeth are angled to encourage movement of said return section toward said second end and inhibit movement of said return section toward said first end.

3. A syringe assembly comprising:
a barrel having a first end and a second end, each of said first and second ends being open;
a needle hub being fluidly coupled to and extending away from said second end;
a plunger extending into said first end, said plunger including an internal end positioned within said barrel and an external end positioned distal to said barrel, a longitudinal axis being defined extending through said external end and said second end;
a needle being fluidly coupled to and extending away from said needle hub;
a grip being attached to said plunger, said grip being configured to be engaged by a person's finger to urge said plunger into said barrel, said grip having an outward portion extending outwardly away from said plunger and away from said longitudinal axis, said outward portion extending generally toward said barrel, said grip having a return portion extending toward said barrel and toward said longitudinal axis, said outward and return portions having an outer surface facing away from said plunger and said barrel, said outer surface being convexly arcuate;
a return section being attached to an end of said return portion opposite of said outward portion, said return section extending toward said first end, said return section having a plurality of first teeth thereon extending toward said barrel; and
a plurality of second teeth being positioned on said barrel, said second teeth being positioned along a line extending between said first and second ends, said second teeth engaging said first teeth, said first and second teeth being angled to encourage movement of said return section toward said second end and inhibit movement of said return section toward said first end.

* * * * *